US012685867B2

(12) United States Patent
Boor

(10) Patent No.: US 12,685,867 B2
(45) Date of Patent: Jul. 21, 2026

(54) SYSTEMS AND METHODS FOR MITIGATING STIMULATION CURRENT SPIKES AND GLITCHES IN NEUROSTIMULATION SYSTEMS

(71) Applicant: Advanced Neuromodulation Systems, Inc., Plano, TX (US)

(72) Inventor: Steven Boor, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 367 days.

(21) Appl. No.: 18/352,546

(22) Filed: Jul. 14, 2023

(65) Prior Publication Data

US 2024/0017073 A1 Jan. 18, 2024

Related U.S. Application Data

(60) Provisional application No. 63/389,539, filed on Jul. 15, 2022.

(51) Int. Cl.
*A61N 1/36* (2006.01)
*A61N 1/05* (2006.01)
(52) U.S. Cl.
CPC ....... *A61N 1/36153* (2013.01); *A61N 1/0534* (2013.01); *A61N 1/36062* (2017.08)

(58) Field of Classification Search
CPC .............. A61N 1/36153; A61N 1/0534; A61N 1/36062; A61N 1/36125
See application file for complete search history.

(56) References Cited

U.S. PATENT DOCUMENTS

| | | | |
|---|---|---|---|
| 9,031,658 B2 | 5/2015 | Chiao | |
| 10,183,168 B2 | 1/2019 | Baru | |
| 11,135,434 B2 | 10/2021 | Boor | |
| 2009/0048643 A1* | 2/2009 | Erickson | A61N 1/378 607/59 |
| 2010/0114205 A1 | 5/2010 | Donofrio | |
| 2013/0018441 A1* | 1/2013 | Childs | A61N 1/36125 607/66 |
| 2014/0117861 A1* | 5/2014 | Finley | H01J 37/32064 315/172 |
| 2023/0144889 A1 | 5/2023 | Park | |

* cited by examiner

*Primary Examiner* — Brian T Gedeon
(74) *Attorney, Agent, or Firm* — Armstrong Teasdale LLP

(57) ABSTRACT

The present disclosure provides systems and methods for mitigating stimulation pulse glitches when a voltage multiplier is stepped during delivery of stimulation current to a patient. An implantable pulse generator (IPG) includes pulse generating circuitry configured to generate stimulation pulses to be applied to a patient at an output of the IPG, voltage multiplier circuitry configured to step an output voltage to an anode of the pulse generating circuitry, and glitch mitigating circuitry configured to mitigate current glitches generated when the output voltage is stepped during generation of a stimulation pulse.

17 Claims, 5 Drawing Sheets

SYSTEMS AND METHODS FOR MITIGATING STIMULATION CURRENT SPIKES AND GLITCHES IN NEUROSTIMULATION SYSTEMS

CROSS-REFERENCE TO RELATED APPLICATIONS

This application claims the benefit of priority to U.S. Provisional Patent Application No. 63/389,539, filed Jul. 15, 2022, the entire contents and disclosure of which are hereby incorporated by reference herein.

A. Field of the Disclosure

The present disclosure relates generally to neurostimulation systems, and more particularly to glitch-mitigation capacitors for substantially reducing a peak amplitude and total charge of current glitches delivered to a patient when a voltage multiplier output is stepped during delivery of a stimulation pulse.

B. Background Art

Neurostimulation is an established neuromodulation therapy for the treatment of chronic pain and movement disorders. Different kinds of electrical spike, pulse stimulation, and neuro-system modulation can be utilized to treat chronic pain or other neurological disorders in parts of the body, such as the brain, spinal cord, and nerves. For example, neurostimulation has been shown to improve cardinal motor symptoms of Parkinson's Disease (PD), such as bradykinesia (slow movement), rigidity, tremor, and postural instability (balance issues). Types of neurostimulation include deep brain stimulation (DBS), spinal cord stimulation (SCS), dorsal root ganglion stimulation (DRG), peripheral nerve stimulation (PNS), motor cortex stimulation (MCS), and repetitive transcranial magnetic stimulation (rTMS).

Neurostimulation systems typically include an implantable pulse generator (IPG). The IPG causes current to flow through lead wires to an electrode across an interface with tissue, and back through the tissue to the IPG and a return electrode. The IPG delivers electrical stimulation to the nervous system.

Burst waveforms have demonstrated success in SCS, and are actively being investigated in DRG stimulation and DBS therapies. A burst waveform typically includes a "burst" including a plurality of pulses each having an associated pulse width, with an intra-burst frequency defining the timing between the plurality of pulses within the burst. The burst repeats at an inter-burst frequency.

In at least some known neurostimulation systems, a voltage multiplier output is stepped up in voltage in real-time during the middle of stimulation pulse. This may improve battery longevity for the IPG, especially when using burst mode stimulation waveforms to deliver spinal cord stimulation (SCS) therapy.

However, when the voltage multiplier output is stepped up, the stimulation waveform may be degraded, and undesirable glitches of current may be briefly delivered through the electrode leads to a patient. These current glitches may be caused by parasitic capacitances between the IPG system ground (GND) and the leads, or the IPG case and the electrode select switches.

Although the current glitches are relatively brief in duration (lasting only ~1 microsecond (μs)) and typically deliver a minimal amount of charge to the patient, they may still impact stimulation therapy integrity (especially for DBS applications, where the current glitches may facilitate therapeutic side-effects). Accordingly, It would be desirable to mitigate the impact of such current glitches when stepping up the voltage of a voltage multiplier.

BRIEF SUMMARY OF THE DISCLOSURE

In one embodiment, the present disclosure is directed to an implantable pulse generator (IPG) for use in a neurostimulation system. The IPG includes pulse generating circuitry configured to generate stimulation pulses to be applied to a patient at an output of the IPG, voltage multiplier circuitry configured to step an output voltage to an anode of the pulse generating circuitry, and glitch mitigating circuitry configured to mitigate current glitches generated when the output voltage is stepped during generation of a stimulation pulse.

In another embodiment, the present disclosure is directed to a neurostimulation system. The neurostimulation system includes an implantable stimulation lead including a plurality of contacts, and an implantable pulse generator (IPG) communicatively coupled to the implantable stimulation lead. The IPG includes pulse generating circuitry configured to generate stimulation pulses to be applied to a patient through the implantable stimulation lead, voltage multiplier circuitry configured to step an output voltage to an anode of the pulse generating circuitry, and glitch mitigating circuitry configured to mitigate current glitches generated when the output voltage is stepped during generation of a stimulation pulse.

In yet another embodiment, the present disclosure is directed to a method of applying neurostimulation. The method includes generating, using an implantable pulse generator (IPG), a pulse to be delivered to a patient, stepping an output voltage to an anode of the IPG while the pulse is being delivered to the patient, and mitigating, using glitch mitigation circuitry, a current glitch generated by the stepped output voltage.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
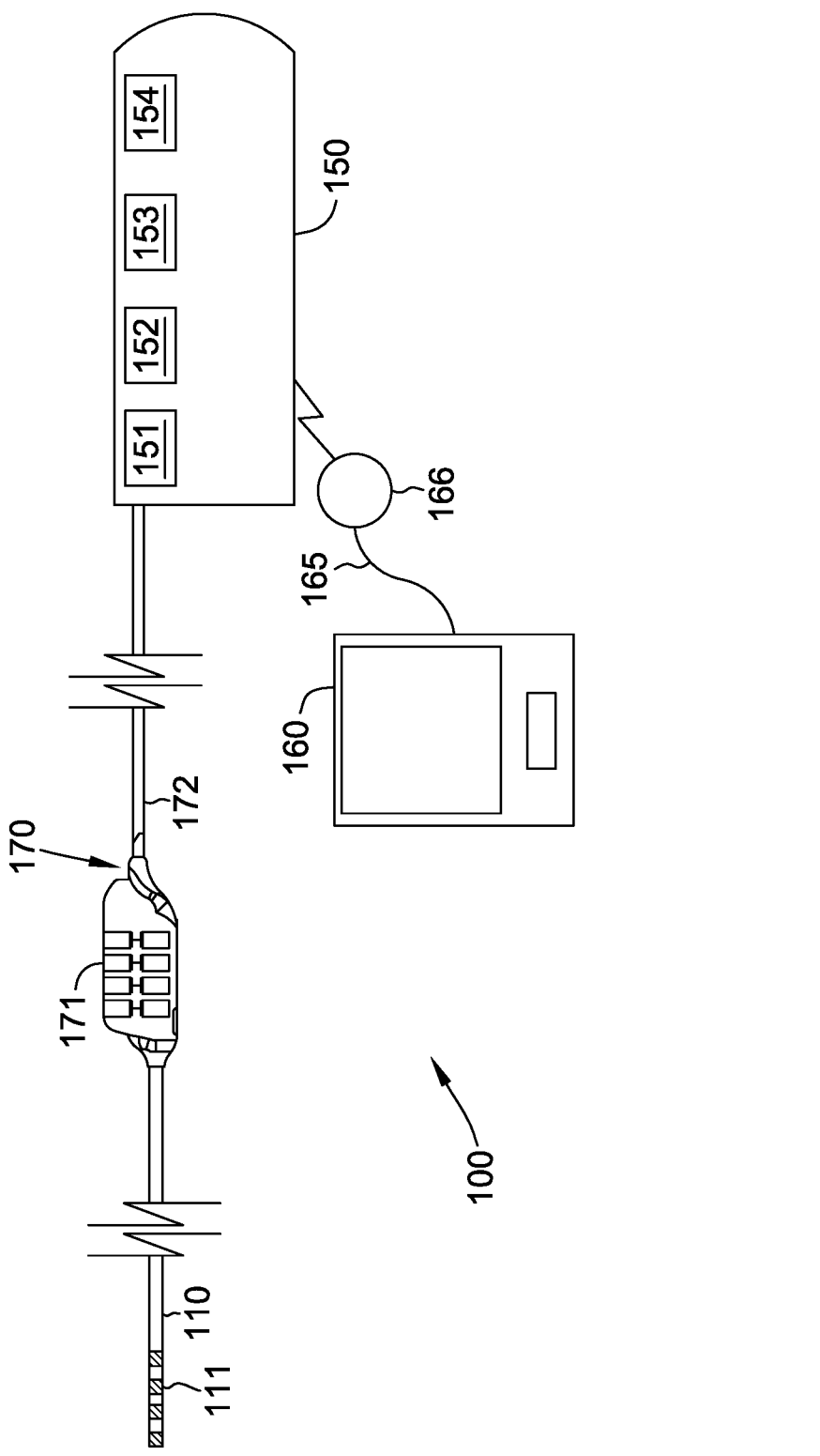
FIG. 1 is a schematic view of one embodiment of a stimulation system.

The present disclosure provides systems and methods for mitigating stimulation current spikes and glitches. An implantable pulse generator (IPG) includes pulse generating circuitry configured to generate stimulation pulses to be applied to a patient at an output of the IPG, voltage multiplier circuitry configured to step an output voltage to an anode of the pulse generating circuitry, and glitch mitigating circuitry configured to mitigate current glitches generated when the output voltage is stepped during generation of a stimulation pulse.

In an IPG system, stepping a voltage, for example, during the middle of a stimulation current pulse, decreases average current drawn from the battery of an implantable pulse generator, thus increasing the longevity of the battery. However, stepping the voltage may result in current glitches. Accordingly, the systems and methods described herein enable mitigating glitches that can cause therapeutic side-effects. This allows for a reduced peak amplitude and total charge delivered to a patient. The systems and methods described herein also allow for a multiplier step to flow through a glitch-mitigation (GM) capacitor network rather than through patient tissue.

The embodiments described herein use GM capacitors to substantially reduce a peak amplitude and total charge of current glitches that may otherwise be delivered to a patient when a voltage multiplier (VMULT) output is stepped during a stimulation pulse. Two of the techniques described herein for reducing the effect of current glitches are i) using an off-chip GM capacitor components, and ii) using an entirely integrated circuit solution (i.e., including all components on the same chip as stimulation control application specific integrated circuits (ASICs)).

Neurostimulation systems are devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) which is often used to treat chronic pain such as Failed Back Surgery Syndrome (FBSS) and Complex Regional Pain Syndrome (CRPS).

Neurostimulation systems generally include a pulse generator and one or more leads. A stimulation lead includes a lead body of insulative material that encloses wire conductors. The distal end of the stimulation lead includes multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted in the patient within a subcutaneous pocket created during the implantation procedure.

The pulse generator is typically implemented using a metallic housing (or can) that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing (or can) that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally, or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the coil of the implantable pulse generator is rectified and regulated to recharge the battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by a user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, stimulation parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The systems and methods described herein facilitate mitigating stimulation current glitches (which may also be referred to as current spikes) when an anode voltage is stepped during the middle of application of a stimulation current pulse. A pattern of stimulation pulses may be stored in a generator (e.g., IPG 150 or an external pulse generator), such that the generator ensures that each pulse is delivered in a specific order, after a specific interval following a previous pulse, with each pulse having a specific amplitude and duration. The mitigation devices described herein are generally implemented during delivery of the stimulation pulses, and may provide improved stimulation in DBS, SCS, peripheral nerve stimulation, and DRG stimulation systems.

Figure 2:
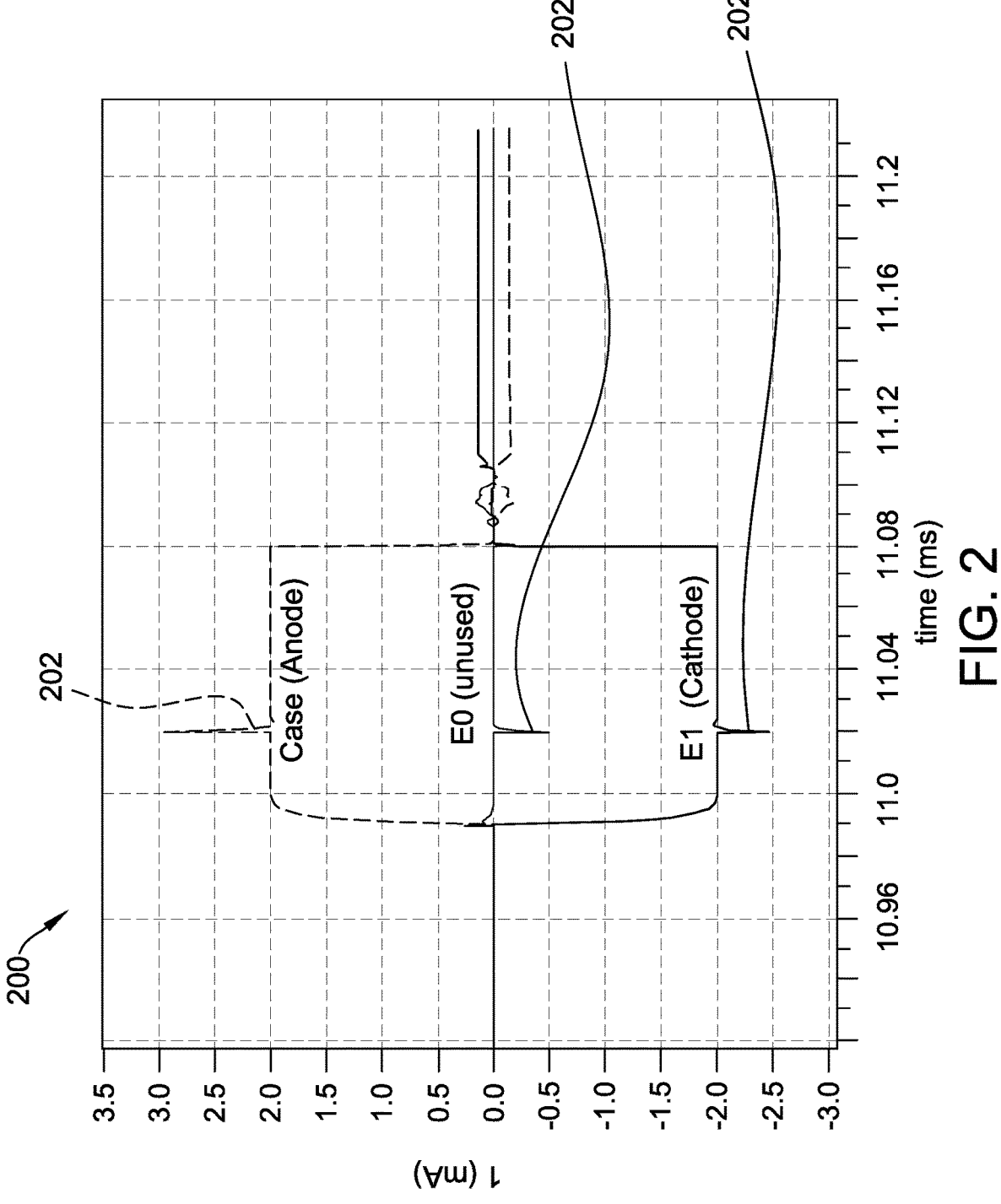
FIG. 2 is a graph illustrating an example of current glitches that may be generated in a DBS system when a voltage multiplier output is stepped by 1V.

FIG. 2 is a graph 200 illustrating an example of current glitches that may be generated in a DBS system when a voltage multiplier (VMULT) output for driving the anode electrode is stepped by 1 Volt (V) during the middle of a stimulation pulse. In this embodiment, no mitigation circuitry is implemented. Here, the example stimulation pulse has an amplitude of 2 milliamps (mA) and a pulse width of 90 milliseconds (ms).

Stepping the VMULT output during the middle of a stimulation current pulse has appreciable advantages for decreasing the average current drawn from the battery of an IPG, thus increasing the longevity of the battery. An implantable pulse generator implementing such functionality is described, for example, in U.S. Pat. No. 11,154,714 entitled "CAPACITIVE VOLTAGE MULTIPLIER FOR PROVIDING ADJUSTABLE CONTROL DURING A STIMULATION PULSE," which is incorporated herein by reference in its entirety.

However, as shown in FIG. 2, stepping the VMULT output, absent any glitch mitigation circuitry, may result in parasitic capacitances to the IPG system ground from the case and cathode electrode(s) causing relatively large current glitches 202 to occur. These current glitches 202 may flow through to patient tissue. Although these current glitches 202 are relatively short (e.g., on the order of 1 microsecond (μs) in duration), they may still have undesirable impacts on stimulation therapy.

In accordance with the embodiments described herein, glitch mitigation (GM) circuitry may be implemented to suppress such current glitches.

In one embodiment, the GM circuitry includes switches, and either two glitch-mitigation (GM) capacitors ($C_{GM1}$ and $C_{GM2}$) and buffer amplifiers, or a dual-capacitor multiplier, such as two MOSFETS used as current mirrors to provide the necessary transient charge during voltage multiplier stepping for charging the parasitic capacitances that are connected from an IPG case and cathode electrode to an IPG system ground (GND).

The two GM capacitors may be switchably connected appropriately between the anode (which is connected to a VMULT output) and the case/cathode, respectively. The two capacitors have electrically equivalent values which are appreciably larger (e.g., at least ten time times greater) than that of the values of the case/cathode parasitic capacitances, which can each routinely approach or exceed 100 pF in actual IPGs. For example, the case parasitic capacitance to the system ground (GND) for some IPGs has been measured to be >300 pico Farad (pF).

Generally, the appropriate connection of the two GM capacitors via switches will occur only briefly for glitch mitigation. This connection occurs as the VMULT output voltage is stepped. For example, the connection may only be made for a short duration just after the VMULT output is stepped, so that the electrically large GM capacitances do not interfere with delivering the intended therapeutic stimulation current to the patient while the VMULT output is held at a steady output voltage.

Alternatively, for stimulation therapy applications which have large double-layer capacitances ($C_{DL}$) in an electrode-tissue interface (ETI), the two GM capacitors may be continuously connected between the anode and the case/cathode without switching. For example, SCS systems typically have $C_{DL}$ capacitances of ~3 micro Farad (pF).

Continuous connection without switching is possible in SCS therapy scenarios because the two GM capacitors will divert such a small amount of stimulation therapy current away from the patient so as to be essentially negligible (e.g., <1% stimulation current delivery error for $C_{GM}=10$ nF and $C_{DL}=3$ pF in a typical SCS ETI).

Figure 3:
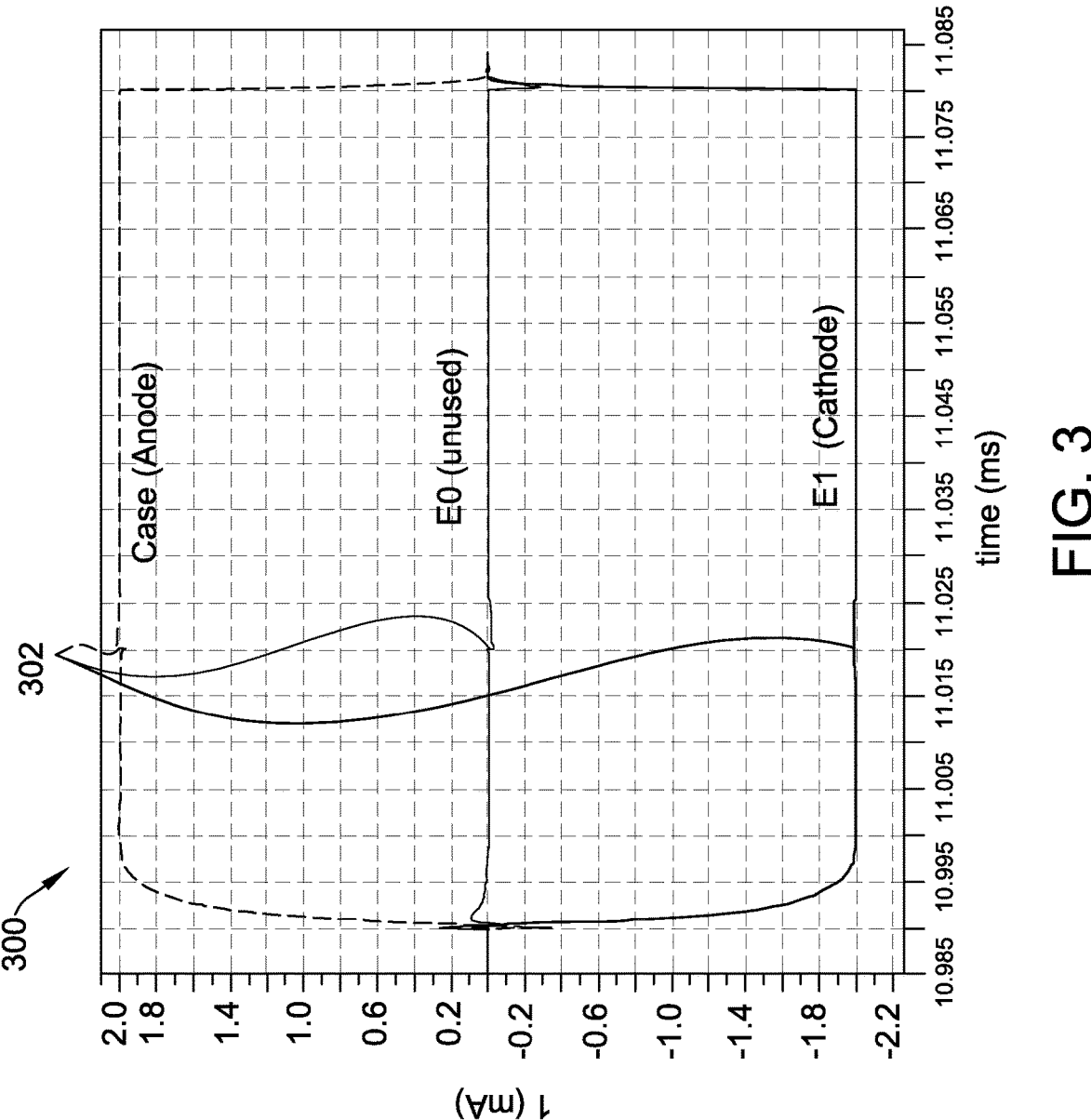
FIG. 3 is a graph illustrating another example of current glitches that may be generated in a DBS system when a voltage multiplier output is stepped by 1V and glitch mitigating circuitry is implemented.

FIG. 3 is a graph 300 illustrating an another example of current glitches that may be generated in a DBS system when a VMULT output is stepped by 1V during a stimulation pulse and glitch mitigating circuitry is implemented. Again, in this example, the stimulation pulse has an amplitude of 2 milliamps (mA) and a pulse width of 90 milliseconds (ms). Notably, as shown in FIG. 3, current glitches 302 are essentially non-existent, and are much smaller than current glitches 202 in the embodiment of FIG. 2.

For example, at the onset of stepping the VMULT output, the switched connection of a pair of electrically large GM capacitors between the VMULT output (i.e., the anode) and the case and cathode electrode can substantially reduce and mitigate the amount of transient charge that will flow through patient tissue (e.g., FIG. 2 as compared to FIG. 3). By using GM capacitors which are electrically much larger (e.g., greater than ten times larger) than the parasitic capacitances of the case and the cathode electrode(s), the vast majority of the transient current needed to charge those parasitics during the stepping of the VMULT output can flow through the GM capacitor network rather than through patient tissue.

This functionality may substantially reduce the peak amplitude, the total charge of the transient current glitches, and the parasitic capacitances flowing through the IPG leads to a patient. These reductions will largely mitigate concerns for degraded stimulation waveforms and for undesirable therapeutic side-effects whenever the VMULT output is stepped, particularly during the middle of delivering a stimulation pulse for therapy.

Referring again to FIG. 3, a substantial reduction in transient current glitches for a VMULT step during a stimulation pulse can be also obtained for electrodes which are not used for stimulation (e.g., the current through electrode E0 in FIG. 3), even though no GM capacitors are connected to them.

The following describes two possible implementations of GM circuitry for mitigating undesirable current glitches whenever the voltage multiplier is stepped during delivery of stimulation current to patient. Those implementations include i) a non-integrated solution via the use of "large valued" discrete component GM capacitors, i.e., on the order of 1 nF or larger (see FIG. 4), and ii) an integrated solution via the use of a dual "capacitor multiplier" circuit (see FIG. 5), which makes the much smaller valued integrated GM capacitors perform electrically like they are of value 1 nF or larger.

The integrated solution advantageously has the capability of operating with less current drawn from the battery than the non-integrated solution (since there is no need for any higher-value (HV) buffer amplifiers). However, the integrated solution may suffer from reacting slower than the non-integrated solution in mitigating the stimulation glitches, as the MOSFET current mirrors may respond slower than the circuitry in the non-integrated solution.

Figure 4:
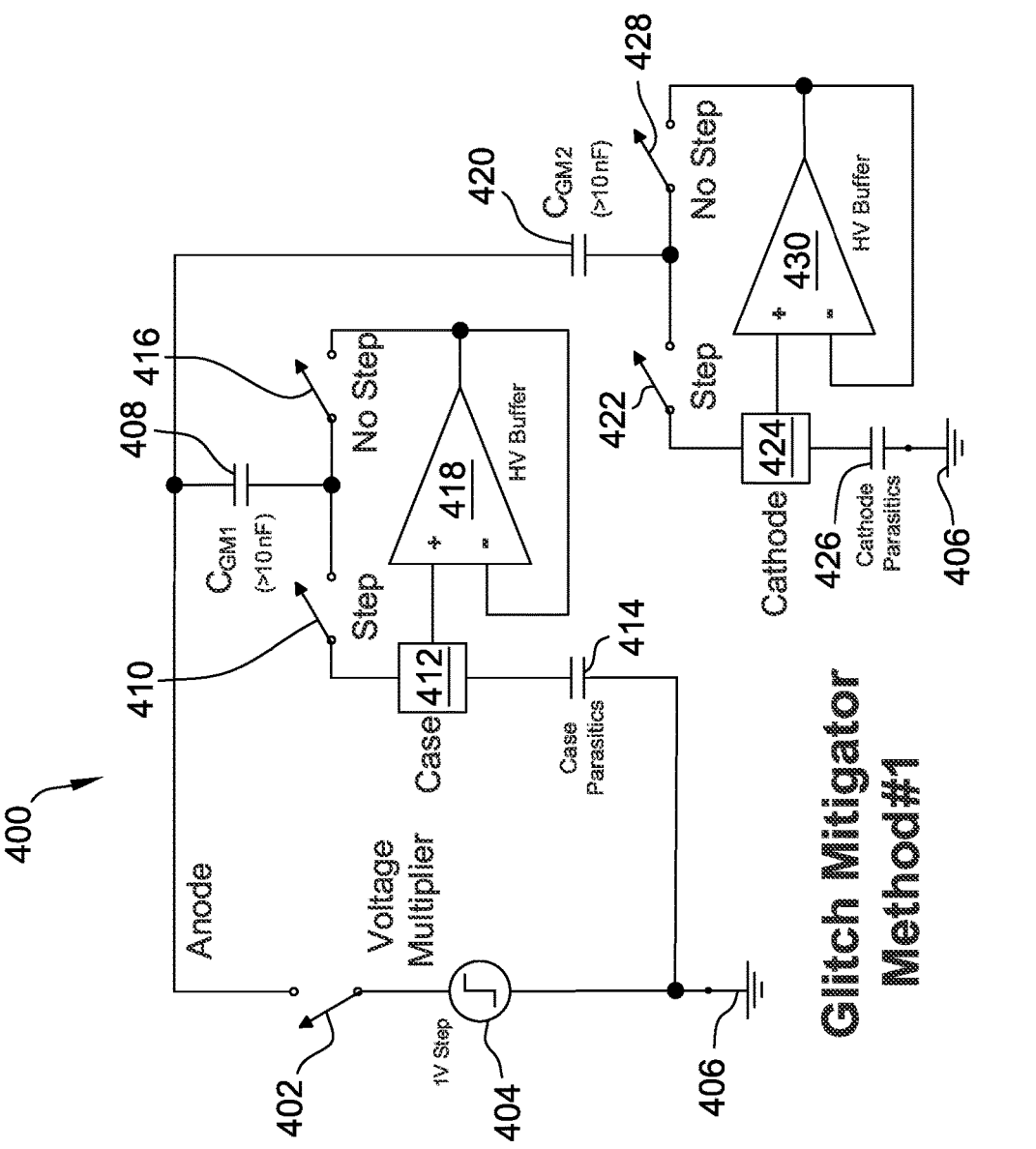
FIG. 4 is a circuit diagram showing a first embodiment of glitch mitigating circuitry that may be used to prevent parasitic capacitances from flowing through the leads of the IPG in FIG. 1.

FIG. 4 is a circuit diagram showing a first embodiment of glitch mitigating circuitry 400 that may be used to prevent parasitic capacitances from flowing through the leads of the IPG in FIG. 1. Circuitry 400 implements a non-integrated solution using off-chip GM capacitor ($C_{GM}$) discrete components, which are "larger-valued" (e.g., on the order of 1 nF or larger).

In FIG. 4, a stimulation pulse is input to the anode of an IPG such as IPG 150 in FIG. 1. A current glitch may occur when a voltage multiplier 404 is stepped (e.g., by 1 V) during the middle of a stimulation pulse. The stimulation glitch may be caused by parasitic capacitances between an IPG system ground 406 and the anode leads, or between IPG case 412 and an electrode select switch 402. Two capacitors and two larger or higher-value (HV) Buffers can be used to mitigate stimulation glitches.

For example, in one embodiment, case 412 is coupled to a positive input of a first HV Buffer 418, a case parasitic capacitor 414, and a first step switch 410. The output voltage of HV Buffer 418 is coupled to its negative input and to a first no-step switch 416. First step switch 410 and first no-step switch 416 are coupled to a first GM capacitor $C_{GM1}$ 408 (e.g., having a capacitance greater than 10 ηF).

Cathode 424 is coupled to a positive input of a second HV Buffer 430, a cathode parasitic capacitor 425, and a second step switch 422. The output voltage of second HV Buffer 430 is coupled to its negative input and to a second no-step switch 428. Second step switch 422 and second no-step switch 428 are coupled to second GM capacitor $C_{GM2}$ 420 (e.g., having a capacitance greater than 10 ηF).

In on embodiment, when voltage multiplier 404 is stepped (e.g., by 1 V) during of a stimulation pulse, switch 402, first step switch 410, and second step switch 422 are all closed.

When first step switch 410 is closed, case 412 and capacitor $C_{GM1}$ 408 are coupled through the anode to voltage multiplier 404 through switch 402. Case 412 is also coupled to the positive input of HV Buffer 418 and to case parasitic capacitor 414, and in series with capacitor $C_{GM2}$ 420.

When second step switch 422 is closed, cathode 424 and capacitor $C_{GM2}$ 420 are coupled through the anode to voltage multiplier 404 through switch 402. Cathode 424 is also coupled to the positive input of HV Buffer 430 and to cathode parasitic capacitor 426, and in series with capacitor $C_{GM1}$ 408.

When the voltage is not being stepped, first no-step switch 416 and second no-step switch 428 are closed.

When first switch 416 is closed, capacitor $C_{GM1}$ 408 is coupled to the output voltage of first HV Buffer 418 and in series with capacitor $C_{GM2}$ 420.

When second no-step switch 428 is closed, capacitor $C_{GM2}$ 420 is coupled to the output voltage of second HV Buffer 430 and in series with capacitor $C_{GM2}$ 420.

Accordingly, first and second step switches 410 and 422, and first and second no-step switches 416 and 428 enable selectively connecting and disconnecting capacitor $C_{GM1}$ 408 and capacitor $C_{GM2}$ 420 between case 412 and cathode 424, respectively.

Figure 5:
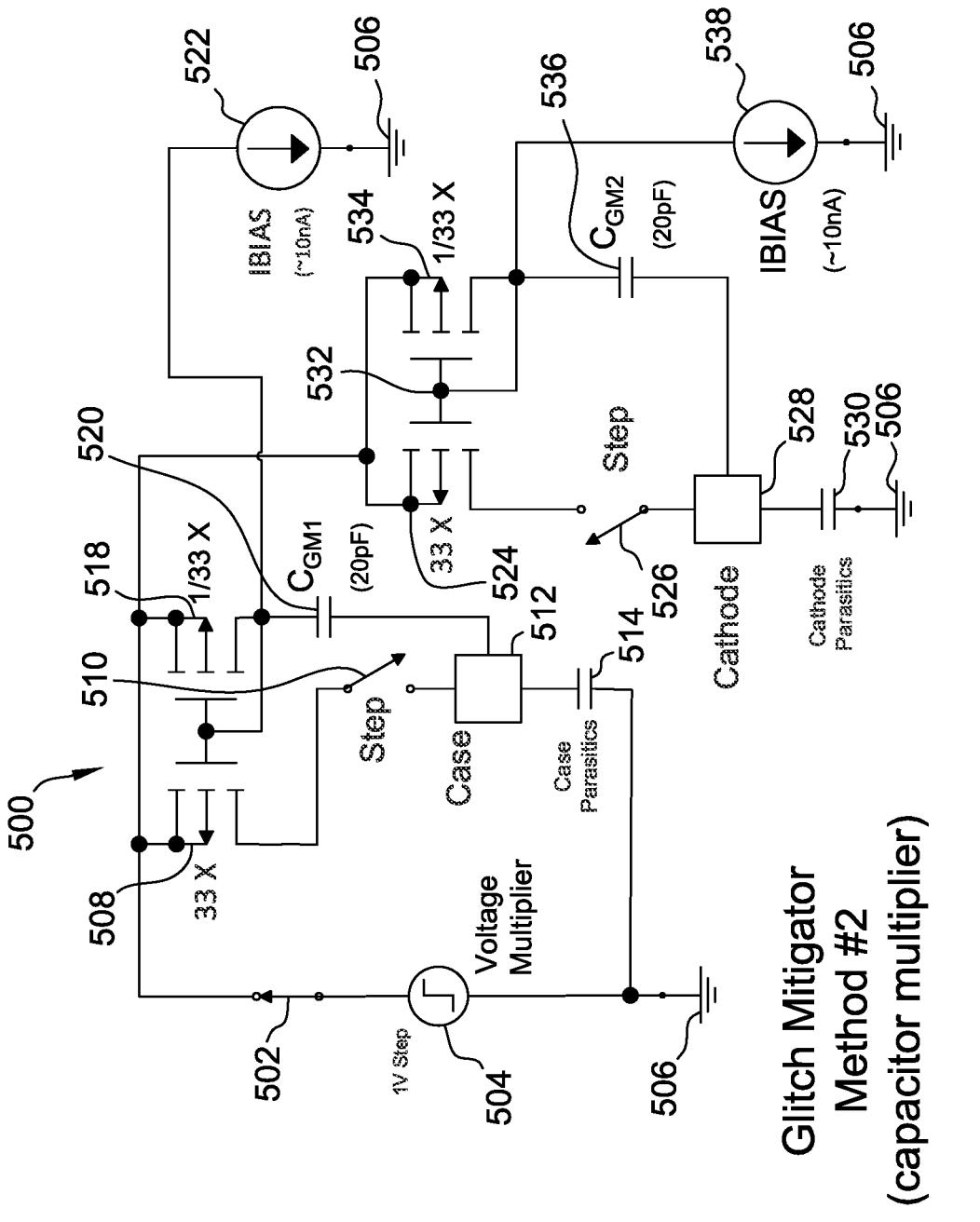
FIG. 5 is a circuit diagram showing a second embodiment of glitch mitigating circuitry that may be used to prevent parasitic capacitances from flowing through the leads of the IPG in FIG. 1.

FIG. 5 is a circuit diagram showing a second embodiment of glitch mitigating circuitry 500 that may be used to prevent parasitic capacitances from flowing through the leads of the IPG in FIG. 1. Circuitry 500 implements an integrated circuit solution where all components are on the same silicon chip as the stimulation control ASIC. In FIG. 5, circuitry 500 is a dual capacitor multiplier circuit, which makes the much smaller-valued integrated GM capacitors perform electrically like they have a capacitance of 1 nF or greater.

Circuitry 500 has the advantageous capability of operating with less current drawn from the battery than circuitry 400 (since there is no need for any HV Buffers). However, circuitry 500 may suffer from reacting slower than circuitry 400 in mitigating stimulation glitches (e.g., the current mirrors may respond slower).

In circuitry 500, a case 512 is coupled to a first step switch 510, a first GM capacitor $C_{GM1}$ 520 (e.g., having a capacitance of 20 pF), and a case parasitic capacitor 514. Case parasitic capacitor 514 and a voltage multiplier 504 are coupled to an IPG system ground 506. Gates of a first p-channel MOSFET 508 (33 X) and a second p-channel MOSFET 518 (1/33 X) are coupled together and to a first IBIAS current source 522 (e.g., providing a current of approximately 10 nA). First IBIAS current source 522 is coupled to ground 506.

A cathode 528 is coupled with a second step switch 526, a second GM capacitor $C_{GM2}$ 536 (e.g., having a capacitance of 20 pF), and a cathode parasitic capacitor 530. Cathode parasitic capacitor 530 is coupled to ground 506 and a second IBIAS current source 538 (e.g., providing a current of approximately 10 nA) is coupled to ground 506. Gates of a third p-channel MOSFET 524 (33 X) and a fourth p-channel MOSFET 534 (1/33 X) are coupled together and to second IBIAS current source 538.

When voltage multiplier 504 is stepped (e.g., by 1 V) during a stimulation pulse, switch 502, first step switch 510, and second step switch 526 are all closed.

When first step switch 510 is closed, case 512 is coupled with the drain of first p-channel MOSFET 508 (33 X).

When second step switch 526 is closed, cathode 528 is coupled with the drain of third p-channel MOSFET 524 (33 X).

The sources of both first MOSFET 508 (33 X) and second MOSFET 518 (1/33 X) are connected in series and coupled to the sources of third MOSFET 524 (33 X) and fourth MOSFET 534 (1/33 X). The sources of MOSFETs 508, 518, 524, and 534 are also coupled to the anode of the IPG.

Accordingly, first and second step switches 510 and 526 enable selectively connecting and disconnecting capacitor $C_{GM1}$ 520 and capacitor $C_{GM2}$ 536 between case 512 and cathode 528, respectively.

The embodiments described herein provide systems and methods for mitigating stimulation current spikes and glitches when an anode voltage is stepped during a stimulation current pulse. An implantable pulse generator (IPG) includes pulse generating circuitry configured to generate stimulation pulses to be applied to a patient at an output of the IPG, voltage multiplier circuitry configured to step an output voltage to an anode of the pulse generating circuitry, and glitch mitigating circuitry configured to mitigate current glitches generated when the output voltage is stepped during generation of a stimulation pulse.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable pulse generator (IPG) for use in a neurostimulation system, the IPG comprising:

a case;

pulse generating circuitry configured to generate stimulation pulses to be applied to a patient at an output of the IPG;

voltage multiplier circuitry configured to step an output voltage to an anode of the pulse generating circuitry; and glitch mitigating circuitry configured to mitigate current glitches generated when the output voltage is stepped during generation of a stimulation pulse to be applied to the patient, wherein the glitch mitigating circuitry comprises:

a first step switch connected to the case;

a second step switch connected to a cathode of the pulse generating circuitry;

a first glitch mitigation capacitor connected to the first step switch, wherein the first glitch mitigation capacitor is connected to the case and the anode when the first step switch is in a closed position; and a second glitch mitigation capacitor connected to the second step switch, wherein the second glitch mitigation capacitor is connected to the cathode and the anode when the second step switch is in a closed position.

2. The IPG of claim 1, wherein the IPG is configured to deliver stimulation pulses to target tissue for spinal cord stimulation (SCS).

3. The IPG of claim 1, wherein the IPG is configured to deliver stimulation pulses to target tissue for deep brain stimulation (DBS).

4. The IPG of claim 1, wherein the glitch mitigation circuitry further comprises first and second no-step switches, wherein the first and second step switches and the first and second no-step switches cooperate to selectively connect and disconnect the first and second glitch mitigation capacitors.

5. The IPG of claim 1, wherein the glitch mitigation circuitry further comprises a first step switch in parallel with the first glitch mitigation capacitor, and a second step switch in parallel with the second glitch mitigation capacitor.

6. The IPG of claim 1, wherein the first and second glitch mitigation capacitors have a capacitance greater than 10 nano Farads.

7. The IPG of claim 1, wherein the first and second glitch mitigation capacitors have a capacitance of approximately 20 pico Farads.

8. A neurostimulation system comprising:

an implantable stimulation lead comprising a plurality of contacts; and an implantable pulse generator (IPG) communicatively coupled to the implantable stimulation lead, the IPG comprising:

a case;

pulse generating circuitry configured to generate stimulation pulses to be applied to a patient through the implantable stimulation lead;

voltage multiplier circuitry configured to step an output voltage to an anode of the pulse generating circuitry; and glitch mitigating circuitry configured to mitigate current glitches generated when the output voltage is stepped during generation of a stimulation pulse to be applied to the patient, wherein the glitch mitigation circuitry comprises:

a first step switch connected to the case:

a second step switch connected to a cathode of the pulse generating circuitry;

a first glitch mitigation capacitor connected to the first step switch, wherein the first glitch mitigation capacitor is connected to the case and the anode when the first step switch is in a closed position; and a second glitch mitigation capacitor connected to the second step switch, wherein the second glitch mitigation capacitor is connected to the cathode and the anode when the second step switch is in a closed position.

9. The neurostimulation system of claim 8, wherein the neurostimulation system is a spinal cord stimulation (SCS) system.

10. The neurostimulation system of claim 8, wherein the neurostimulation system is a deep brain stimulation (DBS) system.

11. The neurostimulation system of claim 8, wherein the glitch mitigation circuitry further comprises first and second no-step switches, wherein the first and second step switches and the first and second no-step switches cooperate to selectively connect and disconnect the first and second glitch mitigation capacitors.

12. The neurostimulation system of claim 8, wherein the glitch mitigation circuitry further comprises a first step switch in parallel with the first glitch mitigation capacitor, and a second step switch in parallel with the second glitch mitigation capacitor.

13. The neurostimulation system of claim 8, wherein the first and second glitch mitigation capacitors have a capacitance greater than 10 nano Farads.

14. The neurostimulation system of claim 8, wherein the first and second glitch mitigation capacitors have a capacitance of approximately 20 pico Farads.

15. A method of applying neurostimulation, the method comprising:

generating, using an implantable pulse generator (IPG), a pulse to be delivered to a patient, wherein the IPG includes a case;

stepping an output voltage to an anode of the IPG while the pulse is being delivered to the patient; and mitigating, using glitch mitigation circuitry, a current glitch generated by the stepped output voltage during generation of a pulse to be delivered to the patient, wherein the glitch mitigation circuitry comprises:

a first step switch connected to the case;

a second step switch connected to a cathode of the pulse generating circuitry;

a first glitch mitigation capacitor connected to the first step switch, wherein the first glitch mitigation capacitor is connected to the case and the anode when the first step switch is in a closed position; and a second glitch mitigation capacitor connected to the second step switch, wherein the second glitch mitigation capacitor is connected to the cathode and the anode when the second step switch is in a closed position.

16. The method of claim 15, wherein the IPG is configured to deliver stimulation pulses to target tissue for spinal cord stimulation (SCS).

17. The method of claim 15, wherein the IPG is configured to deliver stimulation pulses to target tissue for deep brain stimulation (DBS).

* * * * *